United States Patent
Dor et al.

(10) Patent No.: US 9,507,981 B2
(45) Date of Patent: Nov. 29, 2016

(54) ASSOCIATION OF PROCESSED ITEMS WITH PROCESS LOGS

(71) Applicant: HALDOR ADVANCED TECHNOLOGIES LTD, Hod HaSharon (IL)

(72) Inventors: Guy Dor, Rosh Haayn (IL); Dan Zeeli, North York (CA); Ilan Kadosh-Tamari, Ramat Hasharon (IL)

(73) Assignee: HALDOR ADVANCED TECHNOLOGIES LTD, Hod Hasharon (IL)

( * ) Notice: Subject to any disclaimer, the term of this patent is extended or adjusted under 35 U.S.C. 154(b) by 71 days.

(21) Appl. No.: 14/564,119

(22) Filed: Dec. 9, 2014

(65) Prior Publication Data

US 2016/0162714 A1    Jun. 9, 2016

(51) Int. Cl.
| | |
|---|---|
| *G08B 1/08* | (2006.01) |
| *G06K 7/10* | (2006.01) |
| *G06Q 10/08* | (2012.01) |
| *G06Q 50/22* | (2012.01) |

(52) U.S. Cl.
CPC ....... *G06K 7/10366* (2013.01); *G06Q 10/0833* (2013.01); *G06Q 50/22* (2013.01)

(58) Field of Classification Search
CPC ..................... G06K 7/10366; G06K 7/10118; G06K 7/10415; G06K 7/10475; A61L 2/24; A61L 2/28; A61L 2/207; A61L 2/208
USPC ......... 340/539.13, 10.1, 572.8, 539.1, 572.1; 235/385; 435/287.1; 422/26, 292; 707/104.1
See application file for complete search history.

(56) References Cited

U.S. PATENT DOCUMENTS

| | | | | |
|---|---|---|---|---|
| 7,362,228 | B2* | 4/2008 | Nycz | A61F 2/4425 206/363 |
| 7,492,261 | B2* | 2/2009 | Cambre | G06Q 10/08 340/572.1 |
| 7,644,016 | B2* | 1/2010 | Nycz | G06Q 10/0875 340/870.11 |
| 8,925,812 | B2* | 1/2015 | Schmucker | G06Q 10/0875 235/375 |
| 2007/0094303 | A1* | 4/2007 | Zwingenberger | A61L 2/24 |
| 2007/0139202 | A1 | 6/2007 | Austin | |
| 2014/0263633 | A1 | 9/2014 | Schmucker | |
| 2014/0291397 | A1 | 10/2014 | Caputo | |
| 2015/0374868 | A1* | 12/2015 | Bruce | A61L 2/208 422/3 |

FOREIGN PATENT DOCUMENTS

| | | |
|---|---|---|
| EP | 2568077 | 3/2013 |
| WO | 2014/022717 | 2/2014 |

* cited by examiner

*Primary Examiner* — Toan N Pham
(74) *Attorney, Agent, or Firm* — Soroker Agmon Nordman

(57) ABSTRACT

A system for associating processed items with process logs, including a server computer for tracking the items and a tag reader positioned in the vicinity of a device for processing the items; wherein the items are marked with a tag that is readable with a tag reader; wherein the device produces a process log listing a commencement time of the process, a type of process performed and an indication if the process completed successfully; wherein the tag reader records identity information of the items inserted and/or removed from the device for processing; and wherein the process log and identity information are provided to the server computer to associate the processes recorded in the process log with the processed items to form tracking information for an item.

21 Claims, 3 Drawing Sheets

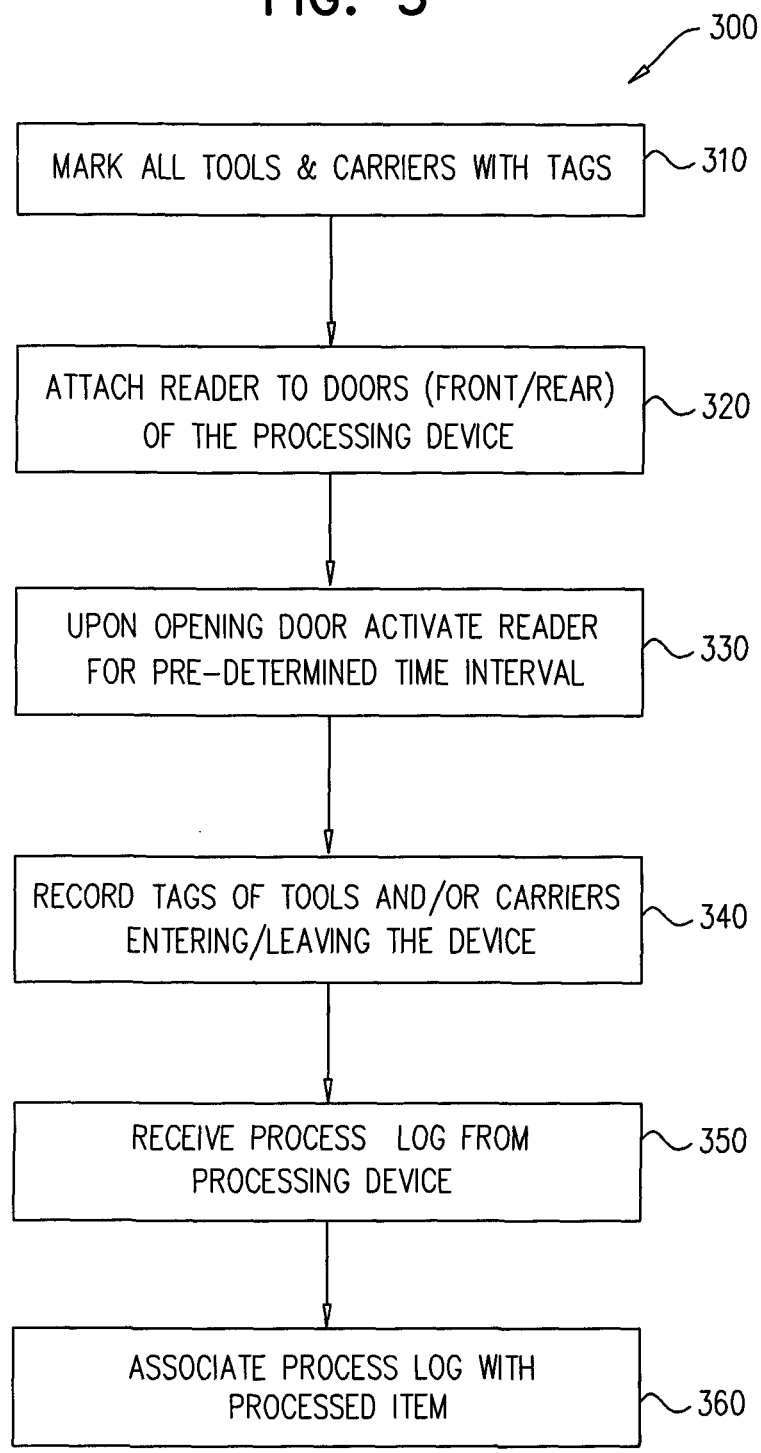

ASSOCIATION OF PROCESSED ITEMS WITH PROCESS LOGS

TECHNICAL FIELD

The present invention relates to a system for tracking tools and machines that process the tools and more specifically to associating machine process logs with the tracked tools.

BACKGROUND

There are many environments in which multiple tools and disposables are used, including for example operation rooms, aircraft hangars, garages, or the like.

An operation room is a facility in which intrusive operations are performed on patients. Typically, multiple people participate in an operation, for example a surgeon, an assistant surgeon, an anesthesiologist, a scrub nurse, and a circulating nurse. The participating personnel members use multiple tools, such as scalpels, forceps, and others, varying according to the surgery being performed.

Intensive efforts are invested in keeping track of all tools and disposables, in order to make sure no tool unintentionally remains inside a patient's body. Therefore careful counting is performed before, during and after the operation.

Counting the tools is a tedious job and requires intensive resources, including mental resources, personnel time and down-time of the operating room. Counting the tools towards the end of an operation also increases the time the patient's body is open with the associated risks.

In addition, counting is not always error-free, and there have been cases in which tools end up being left within the patient's body, causing severe damage or even death.

Another problem relates to the life cycle of tools. For example, the tools used in an operation have to be washed and/or sterilized prior to further usage. Other constraints may relate to maintenance operations required for the tools, for example, a blade may have to be sharpened after every predetermined number of operations in which it is used. In another example, tools that have been used in an operation performed on a patient with a contagious disease may require extra sterilization before further usage, or the like. Making sure that each tool is used and maintained properly also imposes expenses and requires resources, including record keeping, tracking, manual labor and the like.

A computerized system for counting, keeping track of the tools and their maintenance is desirable to enhance dealing with the tools. Such a system needs to uniquely identify each tool. In U.S. Pat. No. 8,193,938 to Halberthal et al dated Jun. 5, 2012 there is disclosed a system and method for keeping track of tools. Identifying tools is performed using a Radio Frequency (RF) identification transducer tag that is attached to the tools.

A tag reader is required to read the tags in a reliable manner. Typically specific shaped containers (or carriers) with built in readers are used for recording placement of tools before and after their use. The containers are equipped with readers having antennas that are tuned to read RFID tags while taking into account the antenna impedance resulting from the design of the container. Tools may be tracked individually or as sets, e.g. the system may verify that a container contains all the tools of a set and keep track of the location of the container.

A set of tools may be placed on a processing rack and inserted into a processing machine, for example a sterilization/washer/disinfection machine. The computerized system needs to be updated with the details of the process and results of the process, so that it may track the life-cycle of the tool. Typically processing machines produce log files recording the performance of a process. However the log file is not associated to a specific tool or set of tools, thus manual updates are required to keep the information related to a specific instance of a tool and/or set of tools up to date.

SUMMARY

An aspect of an embodiment of the disclosure relates to a system and method for associating processed items with process logs. The system includes a computerized server that executes a tracking program for tracking the location and handling of items such as tools used for performing an operation or other purposes. The tools are marked with tags (e.g. RFID tags) so that they can be recorded by tag readers placed at specific locations. The information recorded by the tag readers is transmitted to the server and stored in a database.

The tools also undergo maintenance processes such as cleaning, washing, disinfecting and the like. Each process is performed by a device that is designed to perform the specific process. The device provides the server with a process log listing processes performed by the device. A tag reader is attached to the device or placed near the device to record the identity of the tools inserted into the device for processing. The server receives the time and identity of the tools that were placed in the device and the server identifies matching processes from the process logs that were performed at the times that the tools were inserted. The server then associates the processes with the tools and updates the records of each tool in the database.

In an exemplary embodiment of the disclosure, the tag reader may be placed above a door for inserting the tools into the device. Optionally the device may have a rear door that serves as an exit and another tag reader may be placed above the rear door to track the removal of tools. In some embodiments of the disclosure, the tag reader may be positioned below the door, inside the door or at another location in the vicinity of the door.

In some embodiments of the disclosure the tag reader is activated by opening the door or manually by a user activating a switch. Optionally, the tag reader is activated for a pre-determined length of time or may be active whenever the device is on and not already performing a process. In some embodiments of the disclosure a sensor may be installed inside the device to detect insertion or removal of tools and record their identity.

In some embodiments of the disclosure, the tools may be placed on a carrier and the carrier may be inserted into the device for processing. Optionally, the tag reader attached to the device may only identify the carrier tag, for example by using special tags for carriers. The identity of the tools in the carrier may be known from a tag reader in the carrier identifying the tools placed on it or from previous readings.

There is thus provided according to an exemplary embodiment of the disclosure, a system for associating processed items with process logs, comprising:

a server computer for tracking the items;

a tag reader positioned in the vicinity of a device for processing the items;

wherein the items are marked with a tag that is readable with the tag reader;

wherein the device produces a process log;

wherein the tag reader records identity information of the items inserted and/or removed from the device for processing;
and
wherein the process log and identity information are provided to the server computer to associate processes recorded in the process log with the processed items and to form tracking information for an item.

In an exemplary embodiment of the disclosure, the process log lists a commencement time of the process, a type of process performed and an indication if the process completed successfully. Optionally, the tag reader in the vicinity of the device is attached to the device near an entrance or exit of the device. Optionally, the tag reader in the vicinity of the device is activated by opening a door of the device. In an exemplary embodiment of the disclosure, the tag reader in the vicinity of the device is activated for a pre-determined time interval. Optionally, the device includes an internal sensor that activates the tag reader in the vicinity of the device when detecting insertion or removal of items from the device. In an exemplary embodiment of the disclosure, the tag reader in the vicinity of the device provides a visual indication when activated. Optionally, the tag reader in the vicinity of the device is activated manually. In an exemplary embodiment of the disclosure, the tag reader provides information selected from the group of: time of reading, identification codes identified during the reading process and identification of the tag reader. Optionally, the tracking information of an item includes information selected from the group of: current location, previous locations, processes performed on the item, devices used to perform the processes.

There is further provided according to an exemplary embodiment of the disclosure, a method of associating processed items with process logs, comprising:
  recording tag information of items marked with tags by tag readers;
  transmitting the information to a server computer to track the items;
  placing a tag reader in the vicinity of a processing device to record the tag information of items inserted and/or removed from the processing device for processing;
  receiving process logs from the processing device;
  associating the processes recorded in the process log with the processed items to form tracking information of an item.

In an exemplary embodiment of the disclosure, the process log lists a commencement time of the process, a type of process performed and an indication if the process completed successfully. Optionally, the tag reader in the vicinity of the device is attached to the device near an entrance or exit of the device. In an exemplary embodiment of the disclosure, the tag reader in the vicinity of the device is activated by opening a door of the device. Optionally, the tag reader in the vicinity of the device is activated for a pre-determined time interval. In an exemplary embodiment of the disclosure, the device includes an internal sensor that activates the tag reader in the vicinity of the device when detecting insertion or removal of items from the device. Optionally, the tag reader in the vicinity of the device includes a visual indication when activated. In an exemplary embodiment of the disclosure, the tag reader in the vicinity of the device is activated manually. Optionally, the tag reader provides information selected from the group of: time of reading, identification codes identified during the reading process and identification of the tag reader. In an exemplary embodiment of the disclosure, the tracking information of an item includes information selected from the group of: current location, previous locations, processes performed on the item, devices used to perform the processes.

In an exemplary embodiment of the disclosure, a program for executing the above method is stored on a non-transitory computer medium.

BRIEF DESCRIPTION OF THE DRAWINGS

The present disclosure will be understood and better appreciated from the following detailed description taken in conjunction with the drawings. Identical structures, elements or parts, which appear in more than one figure, are generally labeled with the same or similar number in all the figures in which they appear, wherein:

FIG. 3 is a flow diagram of a method of associating processed items with process logs, according to an exemplary embodiment of the disclosure.

DETAILED DESCRIPTION

Figure 1:
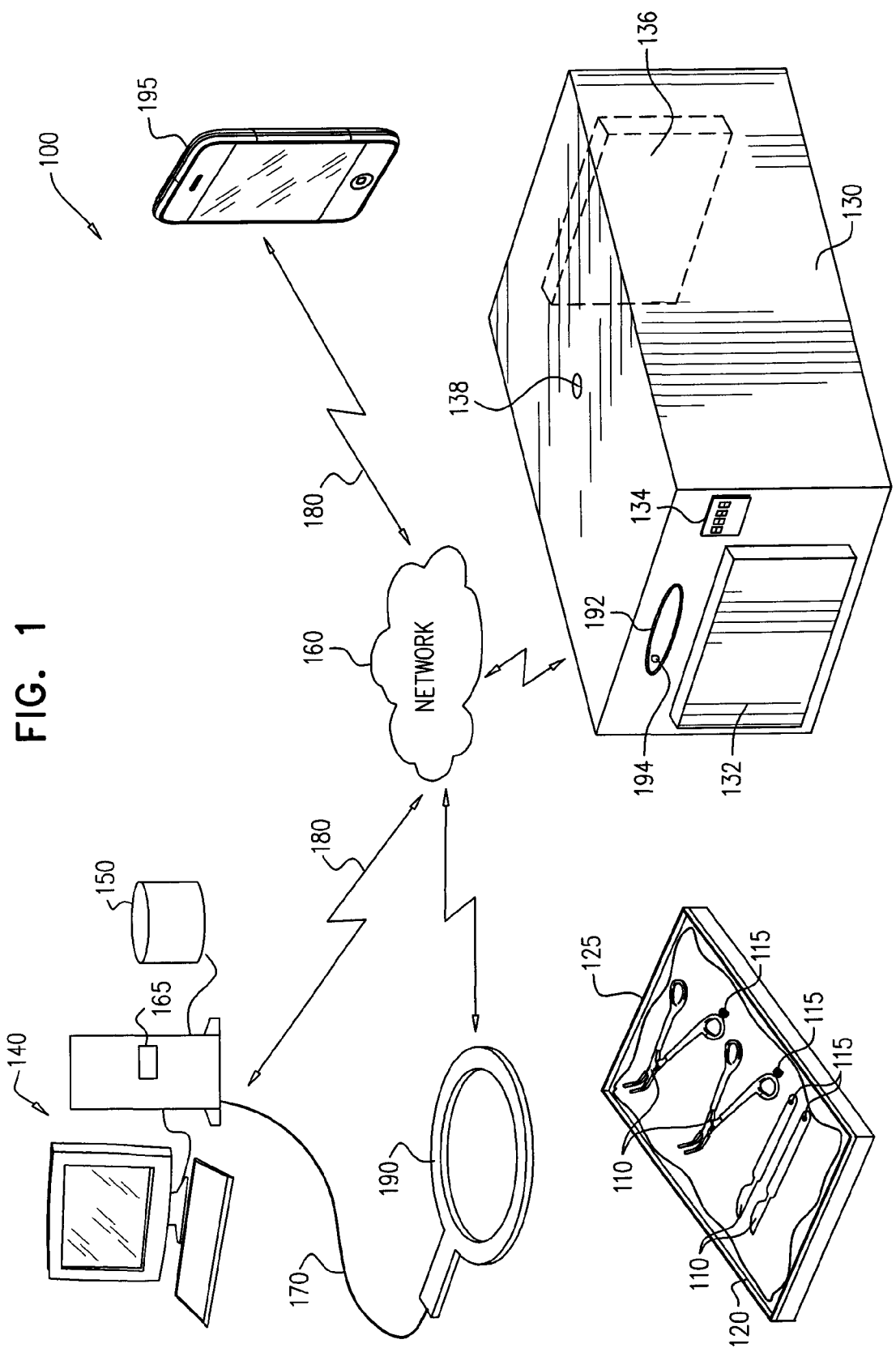
FIG. 1 is a schematic illustration of a system for associating processed items with process logs, according to an exemplary embodiment of the disclosure.

FIG. 1 is a schematic illustration of a system 100 for associating processed items with process logs, according to an exemplary embodiment of the disclosure. In an exemplary embodiment of the disclosure, a server 140 executes a tracking program 165 that keeps track of the location and status of the items including tools 110 and/or tool carriers 120. Optionally, server 140 receives information from one or more tag readers 190 that record the location of tools 110 and/or tool carriers 120 in their vicinity. In some embodiments of the disclosure, the tool carrier 120 may include a tag reader 190 internally for reporting the identity of the tools 110 located on the carrier 120 or the tool carrier 120 may be placed on or near a tag reader 190 to read the tags of the tools on carrier 120. The carrier 120 may also include a carrier tag 125 so that the carrier can be tracked independently. Optionally, the tag reader 190 may transmit the information to server 140 over a communication cable 170 or wirelessly 180 over a communication network 160.

In an exemplary embodiment of the disclosure, one or more processing devices 130 are used to process tools 110, for example processing device 130 can be a machine for sterilizing, washing or disinfecting tools or performing other actions such as manufactured by Belimed Inc (Charleston, S.C.) or Steris Corp. (Mentor, Ohio). Optionally, each device 130 produces a process log with details of the processes performed by the device 130, for example including time, duration, success or failure and other details. In an exemplary embodiment of the disclosure, device 130 includes one or more doors 132, 136 (e.g. a front door 132 and a rear door 136). Optionally, tools 110 are placed on a dedicated rack or on carrier 120, the front door 132 is opened and the rack or carrier 120 is inserted into the device 130. The tools 110 are processed and then removed via the front door 132 or the rear door 136, depending on the design of the device 130 (some device may have one door and some may have a front and rear door). In an exemplary embodiment of the disclosure, device 130 includes a display and/or control panel 134 for controlling the device 130 and for providing indications regarding status and/or progress of the process. Optionally, upon commencement and/or termination of a process the log is transmitted to server 140 to be handled by program 165.

In an exemplary embodiment of the disclosure, a tag reader 192 is installed at front door 132 and/or rear door 136 to record the identification of the rack or carrier 120 and/or the identity of the tools 110 that enter and exit device 130. Optionally, the recorded information is provided to server 140 for analysis by program 165. In an exemplary embodiment of the disclosure, the process logs, tag reader information, tool information are all stored in a database 150 for processing by program 165.

In an exemplary embodiment of the disclosure, server 140 may be a dedicated circuit or a general purpose computer having a processor and memory for executing program 165. Optionally, program 165 may be provided to the general purpose computer on a non-transitory computer medium such as a CD or diskonkey for installing on server 140. During execution program 165 receives information from tag readers 190/192 and/or devices 130. The program may store the information in database 150 and then analyze the information to update a record of the lifecycle of each tool 110. Optionally, remote workstations 195 (e.g. a general purpose computer or other device having a processor and memory such as smart-phones) may be used to query program 165 and receive information regarding the location and status of a specific tool 110, for example if a specific tool is ready for use or if it missed out on an important treatment.

Figure 2:
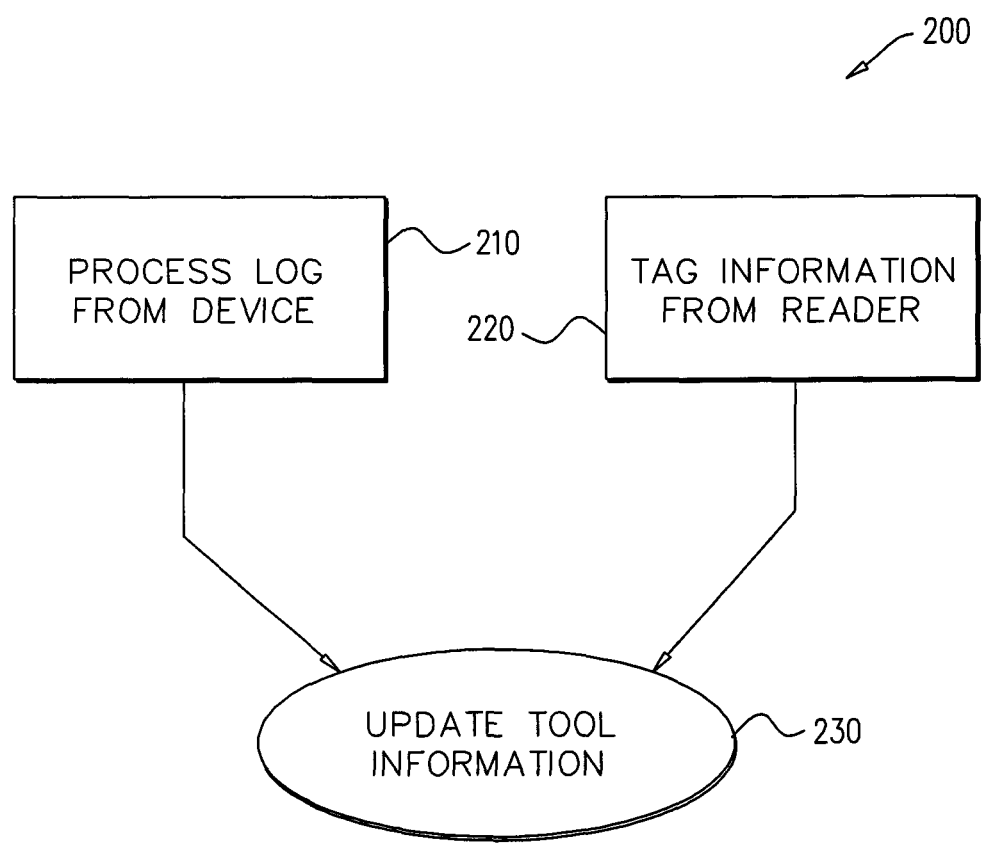
FIG. 2 is a schematic illustration of a processing log and tag reader information combined to update tool tracking information, according to an exemplary embodiment of the disclosure.

FIG. 2 is a schematic illustration of a processing log 210 and tag reader information 220 combined to update tool tracking information 230, according to an exemplary embodiment of the disclosure. In an exemplary embodiment of the disclosure, processing log 210 includes:

1. A machine ID to identify the device 130 that performed the process;
2. A door ID to identify the door through which the items are inserted or removed from the device 130;
3. A start time at which the process commenced;
4. An end time at which the process terminated;
5. A duration representing the difference between the start time and the end time during which the process was performed;
6. An indication as to the type of process/action performed, e.g. washing (ultrasonic, water, air, steam), sterilizing, disinfecting, rack load, rack unload, service run or other processes;
7. A process code indicating if the process was successful, failed, partially successful;
8. A user identity to identify the person that performed the process;
9. A process ID to identify the process performed by the device 130;
10. Physical values such as temperature and pressure used in performing the process. Optionally, the values may be provided as a function of time, so that detailed knowledge of the process the tool underwent is conveyed.

For example the process log 210 may indicate that a rack was loaded however a sterilization process failed, or that a rack was loaded the tools were washed successfully and the rack was removed.

In an exemplary embodiment of the disclosure, tag reader information 220 includes:

1. Time of reading;
2. Duration of reading;
3. Tag identification codes identified during the reading process;
4. Identification of the tag reader 190, 192.

In an exemplary embodiment of the disclosure, program 165 receives processing logs 210 and tag reader information 220 and analyzes the information to determine processes and actions performed on a rack/carrier/tool, for example based on the time and location of the action and the item being processed. Optionally, program 165 then updates the tool information 230 in database 150.

FIG. 3 is a flow diagram of a method 300 of associating processed items with process logs 210, according to an exemplary embodiment of the disclosure. In an exemplary embodiment of the disclosure, tools 110 are marked (310) by attaching a readable tag 115 (e.g. an RFID tag). Optionally, also carriers 120 are marked (310) with a readable tag 125. In some embodiments of the disclosure, carrier 120 may serve as a rack for inserting tools 110 into device 130. Alternatively, tools 110 may be transferred from carrier 120 to a dedicated rack for inserting tools 110 into device 130. Optionally, the rack may also be marked (310) with a readable tag. In an exemplary embodiment of the disclosure, carrier 120 may include a tag reader 190 and record the transfer of the tools 110 out from the carrier 120 to the rack.

In an exemplary embodiment of the disclosure, a tag reader 192 may be attached (320) to doors 132, 136 of device 130. Optionally, the tag reader 192 may be attached to the doors, above the doors, below the doors or in any other position in the vicinity of the doors 132, 136 so that the tags 115, 125 of the tools 110 and/or the carrier 120 can be read while inserting the tools into device 130.

In an exemplary embodiment of the disclosure, upon opening (330) the front door 132 of device 130 the attached reader 192 is activated for a pre-determined time interval to record (340) the tags 115, 125 entering the device. Alternatively, tag reader 192 may be activated all the time or whenever the device has power and is not processing items. In some embodiments of the disclosure, an internal sensor 138 may be installed in device 130 to identify motion or insertion of items. Optionally, sensor 138 activates the attached tag reader 192 to record (340) the insertion of tools 110 and/or carrier 120. Likewise when the rear door 136 is opened a tag reader 192 attached to the rear of the device 130 may be activated to record tags 115, 125 leaving device 130. In some embodiments of the disclosure, a user may activate a switch on control 134 to start and or stop the tag reading process. Optionally, a remote control may be used to activate the switch.

In an exemplary embodiment of the disclosure, server 140 receives (350) the process logs 210 created by the device 130. Optionally, the process logs 210 indicate the time and duration of processes performed by device 130, for example the time and duration of time for all the sterilization cycles performed by the device 130. Optionally, the process log also indicates if a process completed successfully or if there were any problems. In an exemplary embodiment of the disclosure, server 140 also receives (350) from tag reader 192 the time and identity of tools 110 inserted into the device 130 and removed from the device 130. Based on this information server 140 associates (360) a process from the process log 210 with each item that was processed, for example a successful process performed right after the item was inserted into the device 130.

In some embodiments of the disclosure, the display on control 134 may provide an indication while tag reader 192 is scanning for tools 110. Alternatively or additionally, the tag reader 192 may include a visual indication 194, for example a Led light that is lit up or flashes when tag reader 192 is scanning for tags 115, 125.

In some embodiments of the disclosure, the tag reader 192 that is installed on the device 130 may record only the identity of a rack or carrier 120. The identity of the tools 110 on the rack or carrier 120 may be based on prior tracking information of the tools 110, for example by a notification received by server 140 from tag reader 190 of carrier 120. In an exemplary embodiment of the disclosure, the tag reader 192 on the device 130 can be one type of reader, for example a bar-code reader to read bar codes on the rack or carrier, whereas the tag reader 190 of the carrier 120 for recording the deployment of tools 110 onto the carrier may be an RFID reader.

It should be appreciated that the above described methods and apparatus may be varied in many ways, including omitting or adding steps, changing the order of steps and the type of devices used. It should be appreciated that different features may be combined in different ways. In particular, not all the features shown above in a particular embodiment are necessary in every embodiment of the disclosure. Further combinations of the above features are also considered to be within the scope of some embodiments of the disclosure. It will also be appreciated by persons skilled in the art that the present disclosure is not limited to what has been particularly shown and described hereinabove.

We claim:

1. A system far associating processed items with process logs, comprising:
   a server computer for tracking the items;
   a tag reader positioned near a device for processing the items;
   wherein the items are marked with a tag that includes identity information of the item and is readable with the tag reader;
   wherein the device produces a process log;
   wherein the tag reader records identity information of the items inserted and/or removed from the device for processing;
   wherein the tag reader does not write information to the tag;
   wherein the process log and identity information are provided to the server computer to associate processes recorded in the process log with the processed items and to form tracking information for an item; and
   wherein the process log is stored in a database at the server via a communication network.

2. A system according to claim 1, wherein the process log lists a commencement time of the process, a type of process performed and an indication if the process completed successfully.

3. A system according to claim 1, wherein the tag reader in the vicinity of the device is attached to the device near an entrance or exit of the device.

4. A system according to claim 1, wherein the tag reader in the vicinity of the device is activated by opening a door of the device.

5. A system according to claim 1, wherein the tag reader in the vicinity of the device is activated for a pre-determined time interval.

6. A system according to claim 1, wherein the device includes an internal sensor that activates the tag reader in the vicinity of the device when detecting insertion or removal of items from the device.

7. A system according to claim 1, wherein the tag reader in the vicinity of the device provides a visual indication when activated.

8. A system according to claim 1, wherein the tag reader in the vicinity of the device is activated manually.

9. A system according to claim 1, wherein the tag reader provides information selected from the group of time of reading, identification codes identified during the reading process and identification of the tag reader.

10. A system according to claim 1: wherein the tracking information of an item includes information selected from the group of: current location, previous locations, processes performed on the item, devices used to perform the processes.

11. A method of associating processed items with process logs, comprising:
    recording with a tag reader tag information of items marked with tags, including identity information of the items by tag readers;
    placing a tag reader near a processing device to record the tag identity information of items inserted and/or removed from the processing device for processing;
    wherein the tag reader does not write information to the tag;
    transmitting the identity information to a server computer to track the items;
    receiving process logs from the processing device;
    associating the processes recorded in the process log with the processed items to form tracking information of an item; and,
    storing the process log in a database at the server via a computer network.

12. A method according to claim 11, wherein the process log lists a commencement time of the process, a type of process performed and an indication if the process completed successfully.

13. A method according to claim 11, wherein the tag reader in the vicinity of the device is attached to the device near an entrance or exit of the device.

14. A method according to claim 11, wherein the tag reader in the vicinity of the device is activated by opening a door of the device.

15. A method according to claim 11, wherein the tag reader in the vicinity of the device is activated for a pre-determined time interval.

16. A method according to claim 11, wherein the device includes an internal sensor that activates the tag reader in the vicinity of the device when detecting insertion or removal of items from the device.

17. A method according to claim 11, wherein the tag reader in the vicinity of the device includes a visual indication when activated.

18. A method according to claim 11, wherein the tag reader in the vicinity of the device is activated manually.

19. A method according to claim 11, wherein the tag reader provides information selected from the group of: time of reading, identification codes identified during the reading process and identification of the tag reader.

20. A method according to claim 11, wherein the tracking information of an item includes information selected from the group of: current location, previous locations, processes performed on the item, devices used to perform the processes.

21. A non-transitory computer readable storage medium comprising a program for execution on a general purpose computer to perform the method described in claim 11.

* * * * *